(12) United States Patent
Bernard

(10) Patent No.: US 11,701,443 B2
(45) Date of Patent: Jul. 18, 2023

(54) PROCESS FOR TREATING CONTAINER PREFORMS WITH NON-CONTACTING PLASMA TREATMENT

(71) Applicant: SIDEL PARTICIPATIONS, Octeville-sur-Mer (FR)

(72) Inventor: Véronique Bernard, Octeville-sur-mer (FR)

(73) Assignee: Sidel Participations, Octeville-sur-mer (FR)

( * ) Notice: Subject to any disclaimer, the term of this patent is extended or adjusted under 35 U.S.C. 154(b) by 1210 days.

(21) Appl. No.: 16/304,238

(22) PCT Filed: May 18, 2017

(86) PCT No.: PCT/FR2017/051211
§ 371 (c)(1),
(2) Date: Nov. 23, 2018

(87) PCT Pub. No.: WO2017/203136
PCT Pub. Date: Nov. 30, 2017

(65) Prior Publication Data
US 2020/0316240 A1    Oct. 8, 2020

(30) Foreign Application Priority Data

May 25, 2016 (FR) .................................. 1654683

(51) Int. Cl.
*A61L 2/14* (2006.01)
*A61L 2/04* (2006.01)
(Continued)

(52) U.S. Cl.
CPC ..................... *A61L 2/14* (2013.01);
*A61L 2/04* (2013.01); *A61L 2/085* (2013.01);
*A61L 2/12* (2013.01);
(Continued)

(58) Field of Classification Search
CPC ... A61L 2/14; A61L 2/04; A61L 2/085; A61L 2/12; A61L 2/208; A61L 2202/23;
(Continued)

(56) References Cited

U.S. PATENT DOCUMENTS 5,322,651 A   6/1994   Emmer
5,681,521 A   10/1997  Emmer et al.
(Continued)

FOREIGN PATENT DOCUMENTS

CA   2617631 A1 *  2/2007 ............. A01N 25/06
CN   103442985 A *  12/2013 ............... A61L 2/14
(Continued)

OTHER PUBLICATIONS

International Search Report, dated Sep. 1, 2017, from corresponding PCT application No. PCT/FR2017/051211.

*Primary Examiner* — Xiao S Zhao
*Assistant Examiner* — Guy F Mongelli (57) ABSTRACT

Disclosed is a process for treating at least one hollow body made of thermoplastic material, such as a preform or a cap, the treatment process successively including at least the following steps: a first step, consisting in treating at least the inside of the hollow body using hydrogen peroxide; a second step, consisting in heating the hollow body; a third step, consisting in treating the hollow body with plasma in order to reduce the concentration of hydrogen peroxide residues. Also disclosed is a plant for manufacturing containers in which the process is carried out in particular by way of a unit for the plasma treatment of the preforms.

14 Claims, 3 Drawing Sheets

(51) Int. Cl.
*A61L 2/08* (2006.01)
*A61L 2/12* (2006.01)
*A61L 2/20* (2006.01)
*B29C 49/36* (2006.01)
*B29C 49/46* (2006.01)
*B29C 49/68* (2006.01)
*B29L 31/00* (2006.01)

(52) U.S. Cl.
CPC .............. *A61L 2/208* (2013.01); *B29C 49/36* (2013.01); *B29C 49/46* (2013.01); *B29C 49/68* (2013.01); *A61L 2202/23* (2013.01); *B29L 2031/712* (2013.01)

(58) Field of Classification Search
CPC ......... B29C 49/36; B29C 49/46; B29C 49/68; B29C 49/06; B29L 2031/712
See application file for complete search history.

(56) References Cited

U.S. PATENT DOCUMENTS

| | | | |
|---|---|---|---|
| 6,113,840 A | 9/2000 | Emmer et al. | |
| 6,562,281 B1 | 5/2003 | Marchau et al. | |
| 7,101,518 B1 * | 9/2006 | Ko | A61L 2/24 422/298 |
| 7,284,778 B1 | 10/2007 | Pellegatta | |
| 7,806,680 B2 | 10/2010 | Adriansens et al. | |
| 7,867,440 B2 | 1/2011 | Quetel et al. | |
| 8,083,512 B2 | 12/2011 | Adriansens | |
| 8,092,757 B2 | 1/2012 | Adriansens et al. | |
| 9,108,835 B2 | 8/2015 | Hayakawa et al. | |
| 9,593,004 B2 | 3/2017 | Hayakawa et al. | |
| 9,617,135 B2 | 4/2017 | Hayakawa et al. | |
| 9,617,136 B2 | 4/2017 | Hayakawa et al. | |
| 9,861,717 B2 | 1/2018 | Hijikata et al. | |
| 9,896,230 B2 | 2/2018 | Hijikata et al. | |
| 10,112,733 B2 | 10/2018 | Hayakawa et al. | |
| 2007/0110842 A1 * | 5/2007 | Kalemba | B29C 45/006 425/554 |
| 2012/0100238 A1 * | 4/2012 | Humele | B29C 49/42 425/170 |
| 2014/0109519 A1 | 4/2014 | Hayakawa et al. | |
| 2017/0166341 A1 | 6/2017 | Hayakawa et al. | |
| 2017/0166342 A1 | 6/2017 | Hayakawa et al. | |

FOREIGN PATENT DOCUMENTS

| | | | |
|---|---|---|---|
| EP | 0 564 354 A1 | 10/1993 | |
| EP | 0 620 099 A1 | 10/1994 | |
| EP | 2 094 312 B1 | 3/2010 | |
| EP | 2 279 952 A1 | 2/2011 | |
| EP | 2 394 950 A1 | 12/2011 | |
| EP | 2 866 844 B1 | 8/2016 | |
| FR | 2 907 684 A1 | 5/2008 | |
| WO | 99/03667 A1 | 1/1999 | |
| WO | 00/48819 A1 | 8/2000 | |
| WO | 02/22447 A1 | 3/2002 | |
| WO | 03/084818 A1 | 10/2003 | |
| WO | WO-2005102668 A2 * | 11/2005 | ............ B29C 44/04 |
| WO | 2006/136498 A1 | 12/2006 | |
| WO | 2006/136499 A1 | 12/2006 | |
| WO | WO-2012130197 A1 * | 10/2012 | ............... A61L 2/14 |
| WO | WO-2014141894 A1 * | 9/2014 | ............ A61L 2/208 |

* cited by examiner

PROCESS FOR TREATING CONTAINER PREFORMS WITH NON-CONTACTING PLASMA TREATMENT

TECHNICAL FIELD OF THE INVENTION

This invention relates to a process for treatment of hollow bodies and an installation for manufacturing containers that incorporates such a process.

STATE OF THE ART

More particularly, the invention relates to the treatment of hollow bodies that are made of thermoplastic material, such as caps or preforms, respectively used for the manufacture of containers that are known as "sterile" or "ultra-clean."

Such ultra-clean containers are obtained after implementing a decontamination carried out during manufacturing, particularly by chemical means using a sterilizing agent such as hydrogen peroxide ($H_2O_2$).

In an installation for manufacturing sterile or ultra-clean containers made of thermoplastic material, particularly bottles, it is in fact known to use various operations for the purpose of monitoring and controlling the microbiological quality of the manufacturing environment and in particular that of the interior of the containers.

In a general way, it is sought to eliminate all the microbial contaminants (microorganisms), such as bacteria, yeast, mold, etc.

Such microbial contaminants can affect the product packaged in the containers, very particularly in the case of agricultural food products.

To do this, a number of operations are advantageously implemented that aim in particular to obtain a decontamination of the caps as well as the preforms from which the containers are manufactured.

The documents of the state of the art that are cited below and to which reference will be made for more detailed information illustrate in a nonlimiting way examples of operations that more particularly aim to eliminate the above-mentioned microbial contaminants.

The document WO-03/084818 describes, for example, a decontamination treatment by irradiating the neck of preforms by an ultraviolet (UV)-type radiation, before the introduction of said preforms into an oven that forms the heating unit of the installation for manufacturing containers.

Document EP-2,094,312 describes another example of treatment by irradiation with an ultraviolet (UV) radiation which is used in a particular way in an oven to decontaminate at least the outer surface of the preform.

Documents WO-99/03667 and WO-2006/136498 describe examples of decontamination treatment intended more particularly for the interior of a preform, i.e., the inner wall, treated chemically using a sterilizing agent consisting of hydrogen peroxide.

Document WO-2006/136499 describes more specifically a process for decontaminating the interior of a preform in which the sterilizing agent consisting of hydrogen peroxide is deposited by condensation on the inner wall of the preform, in the form of a uniform film of mist.

The preform is then thermally conditioned in an oven to be softened with the aim of then undergoing a transformation into a container by blow molding or by stretch blow molding, the heating of the preform then also having the function of thermally activating the hydrogen peroxide.

At least a portion of the hydrogen peroxide is then evaporated under the effect of the heating, going from the liquid state, in which it is found after having been deposited by condensation, to the gaseous state.

Nevertheless, hydrogen peroxide residue persists in the container later obtained from a thus decontaminated preform, which is not without creating different problems that are detailed below.

The sterilizing agent residue, such as hydrogen peroxide, first of all can cause alterations of the product packaged in the container, particularly by oxidation of the product.

Among the changes, it has been able to be found, for example, depending on the products, changes of taste, of color or else a reduction in the content of Vitamin C in some fruit juice(s).

Now, certain rules that are applicable in the agricultural food field impose maximum values with respect to the presence in a container of sterilizing agent residue such as hydrogen peroxide.

By way of nonlimiting example, the FDA (Food and Drug Administration) in the United States provides, under the terms of Title 21 CFR Part 178.1005 (d) of the U.S. "Code of Federal Regulations," that the concentration of hydrogen peroxide in a container used for the packaging of an agricultural food product must be less than a concentration of 0.5 ppm.

Although a decontamination process such as the one described in the above-mentioned document WO-2006/136499 makes it possible to substantially reduce the amount of hydrogen peroxide used while maintaining the levels of decontamination previously obtained, the fact is that residue is always present with a certain concentration in the finished container.

The document EP 2866 844 describes a method for sterilizing a bottle made of PET comprising a step for introducing hydrogen peroxide into the bottle, a step for introducing hot air into the bottle, and a step for introducing plasma which takes place before or after the step for introducing hydrogen peroxide.

Furthermore, a larger amount of hydrogen peroxide is used for the decontamination of small-capacity (less than 1 L) containers; said containers consequently have a concentration of residue that is generally higher, in proportion to their volume. Now, low-capacity containers have experienced a significant surge in commercial interest in recent years.

As a consequence, solutions are sought that make it possible to reduce the concentration of hydrogen peroxide residue in containers obtained from preforms decontaminated chemically using such a sterilizing agent but also in the caps which, used for closing them, are also chemically decontaminated.

The object of the invention is very particularly to propose a solution to solve all or part of the problems described above and particularly the problems of concentrations of hydrogen peroxide residue in ultra-clean or sterile containers.

BRIEF SUMMARY OF THE INVENTION

For this purpose, the invention proposes a process for treatment of at least one hollow body made of thermoplastic material, said treatment process having successively at least the following steps:

(a) a first step, consisting in treating at least the interior of the hollow body using hydrogen peroxide;

(b) a second step, consisting in heating said hollow body;

(c) a third step, consisting in treating the hollow body with plasma to reduce the concentration of hydrogen peroxide residue there.

According to other characteristics of the invention:

the first step, of treatment, consists in depositing a film of hydrogen peroxide by condensation at least on the interior of the hollow body with the aim of decontaminating it;

the second step, of heating, consists in heating the hollow body, in which hydrogen peroxide is found, to a determined temperature which is higher than the activation temperature of the hydrogen peroxide;

the second step, of heating the hollow body, is achieved by heating means;

during the third step, of treatment, plasma is delivered by at least one nozzle which is positioned in such a way that the plasma alone penetrates the interior of the hollow body;

the free end of the nozzle for injecting the plasma is located at a distance from the hollow body which is less than a centimeter, for example between 0.02 cm and 0.8 cm;

the plasma application time during the third step, of treatment, is less than a second, for example between 0.3 and 0.6 s;

the hollow body is a preform;

the hollow body is a cap.

The invention further proposes an installation for manufacturing containers from preforms made of thermoplastic material, said installation having at least:

one unit for treating the interior at least of the preforms by application of hydrogen peroxide;

one unit for heating the preforms;

one unit for molding containers formed by blow molding or by stretch blow molding from heated preforms;

characterized in that the installation has at least one unit for plasma treatment of the decontaminated preforms which is positioned upstream from the molding unit to reduce the concentration of hydrogen peroxide residue on the interior of the preforms.

Advantageously, the unit for treatment by application of hydrogen peroxide is positioned upstream from the unit for heating the preforms, and the plasma treatment unit is positioned between the heating unit and the molding unit, so that the plasma treatment of the preforms is carried out after they have been previously decontaminated by the hydrogen peroxide in the corresponding treatment unit.

BRIEF DESCRIPTION OF THE FIGURES

Other characteristics and advantages of the invention will be brought out during the reading of the following detailed description, for the understanding of which reference will be made to the accompanying drawings in which.

DETAILED DESCRIPTION OF THE FIGURES

Figure 1A:
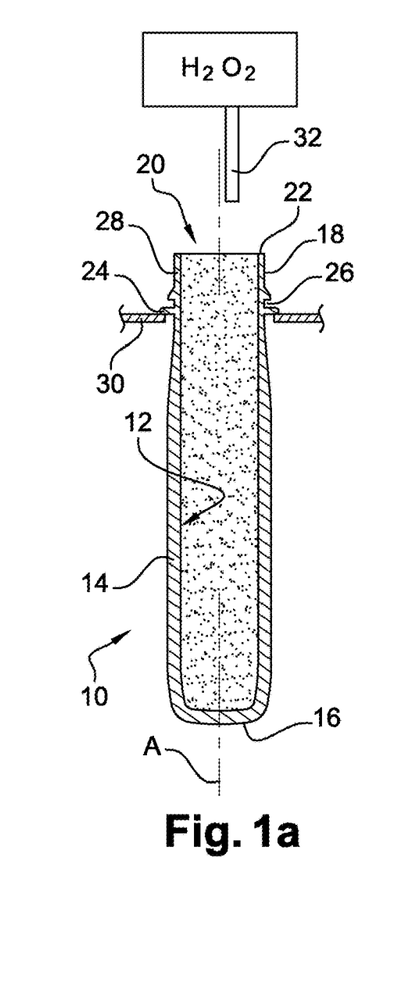
FIGS. 1a, 1b and 1c are views which diagrammatically represent the steps of the treatment process according to the invention to treat at least one preform made of thermoplastic material intended for the manufacture of a container and which illustrate successively the treatment of the interior at least of the preform with hydrogen peroxide with the aim of decontaminating it, the heating of the body of the preform and a plasma treatment of at least a portion of the interior of the preform so as to reduce the concentration of hydrogen peroxide residue there.
Figure 1B:
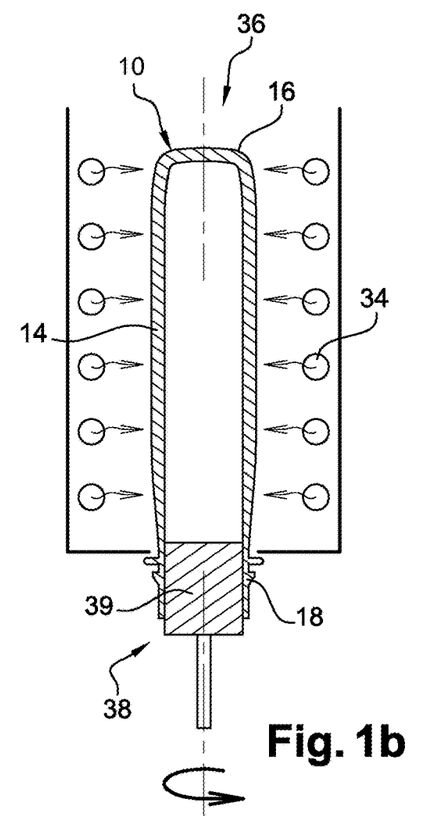
Figure 1C:
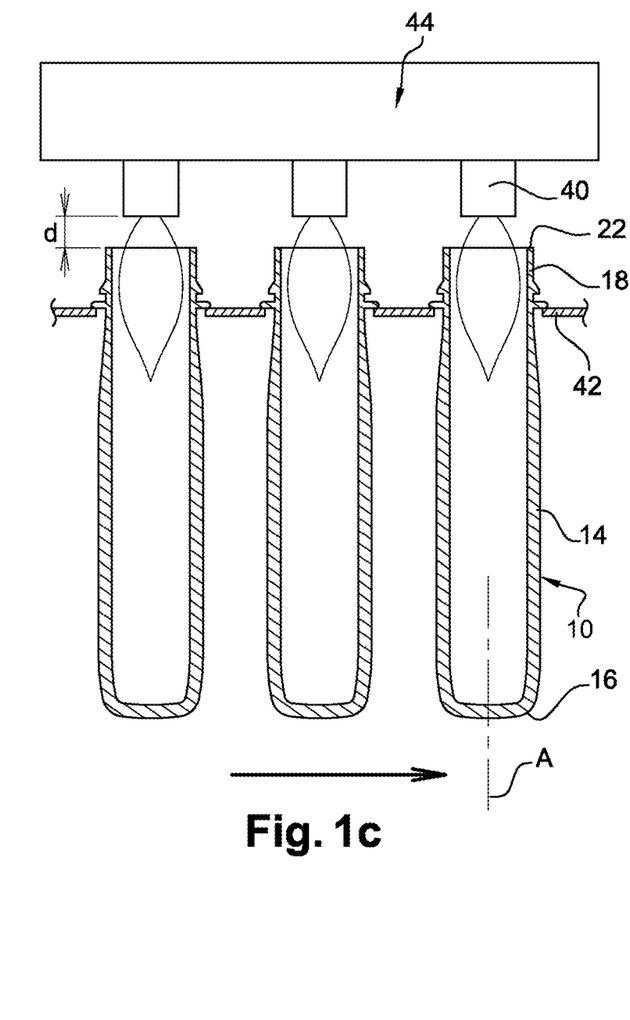

Represented in FIGS. 1a to 1c is a hollow body formed by a preform 10 made of thermoplastic material to illustrate a first example of application of the treatment process according to the invention.

The preform 10 is obtained by molding by injection of plastic material and has characteristics (dimensions, distribution of the material, etc.) which are determined by the finished container to be obtained, in particular its shape or else its capacity.

Such a preform 10 is used for the manufacture of different types of containers (bottles, flasks, jars, etc.) which are particularly, but not exclusively, intended to be used for the packaging of agricultural food products.

The preform 10 has an inner surface 12 delimited by a body 14 closed at one end by a bottom 16 and which, at the other end, has a neck 18 delimiting an opening 20, generally circular, for access to the interior of the preform 10.

The preform 10 has a main axis A which extends axially from the bottom 16 to the neck 18.

The neck 18 of the preform 10 has its final shape at the end of the injection manufacturing of the preform and corresponds to the neck of the finished container, an edge 22 of the neck (or rim) delimiting the circumference of the opening 20 which constitutes the only access to the interior of the preform 10.

The inner diameter of the preform 10 can vary over the height along the main axis A of the preform, i.e., between the neck 18 and the bottom 16.

In the example shown in FIGS. 1a to 1c, the neck 18 has a collar 24 which extends projecting radially outward and an annular groove 26 which, adjacent to said collar 24, is intended to receive subsequently a tamper-proof ring.

Such a ring is intended to guarantee to the consumer the integrity of the filled finished container prior to a first opening.

Preferably, the neck 18 has a thread 28 intended to make it possible for the final container to be closed with a cap having a complementary thread.

For its conveyance, the preform 10 can be taken by the interior of the neck 18 by holding means (this is particularly the case in the heating ovens where the preforms are carried by mandrels inserted into the opening of the neck 18) but the collar 24 of the preform 10 or the annular groove 26 are also often used.

As illustrated in FIG. 1a, the preform 10 is supported by conveying means 30 which work with a portion of a lower surface of the collar 24.

In a known way, the conveying means 30, for example, consist of rails or else a plate provided with notches belonging to a transfer wheel or else arms equipped with gripping clamps.

As explained in the introduction, solutions are sought to manufacture ultra-clean (or sterile) containers having a reduced concentration of hydrogen peroxide.

The presence of hydrogen peroxide in the containers results from the use of hydrogen peroxide as sterilizing agent to decontaminate, on the one hand, the caps and, on the other hand, at least the interior of the preforms which are treated prior to their transformation into containers.

The invention proposes a process for treating at least one hollow body made of thermoplastic material, such as a preform or a cap, to reduce the concentration of hydrogen peroxide in a finished container, i.e., closed by a cap.

The process for treating the hollow body made of thermoplastic material has successively at least the following steps:

(a) a first step, consisting in treating at least the interior of the hollow body using hydrogen peroxide;
(b) a second step, consisting in heating said hollow body;
(c) a third step, consisting in treating the hollow body with plasma to reduce the concentration of hydrogen peroxide residue there.

Thus, the treatment process according to the invention has at least one step for decontamination of at least the interior of the hollow body using hydrogen peroxide.

In the example of application represented in FIGS. 1a, 1b and 1c, the hollow body consists of a preform 10 made of thermoplastic material, such as PET.

The preform 10 is intended to be transformed into a container by blow molding or by stretch blow molding in a mold after having been previously thermally conditioned so as to soften its thermoplastic material.

In this first example of application, a decontamination of at least the interior of the preform 10 as a result of hydrogen peroxide is initiated, i.e., the decontamination of the entire inner surface 12 that is intended later to be in contact with the packaged product once the container is formed.

The decontamination step of said treatment process has at least one first step (a), of treatment with hydrogen peroxide, and one second step (b), of heating the preform 10.

Preferably, as illustrated in FIG. 1a, the first step (a), of treatment with the aim of decontaminating it, consists in depositing hydrogen peroxide by condensation at least on the interior of the preform 10.

The hydrogen peroxide is introduced on the interior of the preform 10 in the form of a gaseous mixture also having hot air. The hydrogen peroxide in the liquid state is first of all evaporated then mixed with the hot air to be routed to the preform 10 to be treated.

When said hot mixture having the hydrogen peroxide comes into contact with the inner surface 12 of a preform 10 having a lower temperature (for example at ambient temperature), a condensation phenomenon will then be produced and result in the depositing of a uniform film of mist over the entire inner surface 12.

In a nonlimiting way, the film of hydrogen peroxide mist deposited by condensation on the entire inner surface 12 of the preform 10 has been marked by a multitude of dots.

Reference will advantageously be made to the previously-cited documents WO-2006/136498 and especially WO-2006/136499 for more ample details on the decontamination of a preform 10 according to this process for decontamination of preforms.

This decontamination process is, moreover, commercially exploited by the Applicant under the name "Predis™" (registered trademark).

In FIG. 1a, in a nonlimiting way, a single preform 10 has been represented to illustrate step (a) only.

Step (a), of treatment, can, however, be simultaneously or almost simultaneously completed in one or more preforms respectively treated while remaining stationary or while being in motion relative to means for injecting the hydrogen peroxide. As illustrated in FIG. 1a, the means for injecting the hydrogen peroxide have at least one injection nozzle 32.

Preferably, the preform 10 occupies a stationary position relative to the nozzle 32 for injecting the hydrogen peroxide which is introduced axially on the interior of the preform 10 through the opening 20 delimited radially by the edge 22 of the neck 18.

Advantageously, the injection nozzle 32 is offset radially in relation to the axis A of the preform 10 so that the main axis of the nozzle 32 is not coaxial with the axis A of the preform 10.

In a variant, not shown, the hydrogen peroxide is injected into the preform 10 by more than one injection nozzle 32. The hydrogen peroxide is, for example, injected in line, successively by several adjacent nozzles relative to which the opening 20 of the preform 10 undergoes a relative movement. In other words, the preforms 10 can be moved in front of the nozzle or nozzles and/or vice versa.

The second step (b), of heating, consists in heating the hollow body made up of the preform 10.

The step (b), of heating, has at least the function of thermally activating the hydrogen peroxide previously injected during the step (a) so as to obtain the decontamination effect.

The step (b), of heating, consists in heating the preform 10 to a temperature which is higher than the activation temperature of hydrogen peroxide.

The activation temperature of hydrogen peroxide is about seventy degrees Celsius (70° C.).

The hydrogen peroxide deposited by condensation on the inner surface 12 of the preform 10 advantageously forms a uniform film of mist and consequently is at least in part in the liquid state.

The heating according to the step (b) causes an evaporation of at least a portion of the film, in which the concentration of hydrogen peroxide will thus grow, and then increasing the decontamination effect obtained.

Preferably, when the hollow body is a preform 10, the second step (b), of heating, also has the function of heating the body 14 of the preform 10 to a molding temperature to make possible its subsequent transformation into a container.

Although the molding temperature varies as a function of the preforms 10, the molding temperature is generally between ninety-five degrees Celsius (95° C.) and one hundred thirty-five degrees Celsius (135° C.).

The molding temperature of the preform 10 is therefore higher than the activation temperature of hydrogen peroxide.

The second step (b), of heating the preform 10, is achieved by heating means 34.

The heating means 34 are, for example, infrared radiation (IR) heating means or laser-type means or else microwave heating means. In a variant, the heating means 34 are hot air heating means.

In the case of preforms 10, the step (b), of heating, is completed in at least one oven 36 which is provided with such heating means 34.

Preferably, the heating of the body 14 of the preform 10 is completed in a so-called "neck down" position so as to avoid heating the neck 18 by convection.

In a known way, the neck 18 has its final shape and must not be heated unlike the body 14; the oven 36 advantageously has cooling means (not shown) for the neck 18 of the preforms 10. The cooling means, for example, consist of a filtered air flow which is placed in circulation in the oven 36 to cool at least the necks 18 of the preforms 10.

In an oven 36, the preforms 10 are conveyed by a conveying device 38 having gripping means 39 for each preform 10, for example by the interior of the neck 18.

Advantageously, the gripping means 39 are also able to drive each preform 10 in rotation on itself around its axis A, simultaneously with the movement through the oven 36 following a given heating path.

Such a device 38 for conveying preforms in an oven and means 39 for gripping preforms are, for example, described in the document WO-A-00/48819 to which reference will be made for more ample details.

In the same way, reference can be made by way of nonlimiting examples of ovens for heating preforms to the documents EP-A-0,620,099 and EP-A-0,564,354.

The third step (c), of treatment, of the process according to the invention consists in using a plasma to reduce the concentration of hydrogen peroxide present on the interior of the preform 10 at the end of the previously-implemented decontamination step.

According to the invention, during the third step (c), of treatment, a plasma is injected by at least one injection nozzle 40 so as to be introduced into the interior of the preform 10.

Preferably, the nozzle 40 for injecting the plasma is positioned so that the plasma alone penetrates the interior of the hollow body formed, in this first example, by the preform 10.

In a variant, not shown, the nozzle 40 for injecting the plasma penetrates the interior of the hollow body formed, in this first example by the preform 10, to introduce the plasma there.

Advantageously, the free end of the nozzle 40 for injecting the plasma is located at a distance "d" from the edge 22 of the neck 18 of the preform 10 which is less than one centimeter (1 cm). The distance "d" between the edge 22 of the neck 18 of the preform 10 and the end of the nozzle 40 is, for example, between 0.02 cm and 0.8 cm.

As illustrated in FIG. 1c, the step (c), of treatment, is completed simultaneously in several preforms 10 which are thus treated in line by a series of nozzles 40 positioned beside one another on a path.

Preferably, the preforms 10 are moved relative to the nozzles 40 by a conveying device 42, such as a plate that is mounted to move in rotation, along the arrow shown in FIG. 1c.

The plasma application time during the third step (c), of treatment, is less than a second. Preferably, plasma application time during this third step (c) is, for example, between 0.3 s and 0.6 s.

As a result of the third step (c), of plasma treatment, at least a portion of the hydrogen peroxide remaining on the interior of the preform 10 after the decontamination operation of the steps (a) and (b) is eliminated.

The plasma after reacting makes it possible to break down the hydrogen peroxide ($H_2O_2$) into two harmless components, respectively water ($H_2O$) and dioxygen ($O_2$):

$$2H_2O_2 \rightarrow 2H_2O + O_2$$

The plasma treatment time for reducing significantly the residual amount of hydrogen peroxide is advantageously less than one second (1 s).

The step (c), of plasma treatment, makes it possible to reduce at least by two the concentration of hydrogen peroxide in the container obtained from a preform 10.

The plasma introduced through the opening 20 of the neck 18 will in particular act on the hydrogen peroxide present on the inner surface 12 in the area of the neck 18 of the preform 10.

Now, the concentration of hydrogen peroxide in the area of the neck 18 is generally greater than on the rest of the inner surface 12 of the preform 10, particularly in the area of its body 14.

This results from the fact that, during the step (b), of heating, the necks 18 of the preforms 10 are not heated in the oven 36 unlike the body 14.

During the third step (c), the plasma introduced into the interior of the preform 10 can consequently treat only one part of the inner surface 12 of the preform 10, bearing in mind that the concentration of hydrogen peroxide residue is considered on the entire container obtained from such a preform 10.

As shown diagrammatically in FIG. 1c, the plasma is, for example, produced by a device 44 which is able to supply plasma to one or more nozzles 40.

Preferably, the plasma is of the "atmospheric" type, i.e., whose jet is sprayed in the open air.

The plasma is obtained by means of an electrical discharge and a gas which advantageously consists of at least air. The choice of air has advantages, particularly a reduced cost because of its great availability.

By way of nonlimiting example, an atmospheric pressure cool plasma generator is marketed by the PlasmaTreat® company under the name "OPENAIR™."

Advantageously, such an atmospheric pressure cool plasma is homogeneous, i.e., steady over time and uniform over the surface, potential-free (since the torch is grounded, an electrically de-energized plasma jet is obtained), and of high intensity.

Preferably, the plasma used is obtained from air, in a variant from a mixture of gas made up at least partly of air.

In a variant, the plasma is obtained from at least one gas other than air (or a mixture of gas), advantageously an inert gas such as nitrogen, argon or helium.

The type of nozzle 40 used to spray the plasma can vary as a function particularly of the type of hollow bodies treated, very particularly in this first example of application of the type of preforms 10.

The choice of the nozzle 40 for spraying the plasma is also determined depending on whether or not the plasma is applied from the exterior of the preform 10 or else depending on whether or not the preform 10 is in motion relative to at least one nozzle 40.

In an alternate manner, several types of nozzles are used to treat the same preform 10 so as to treat more specifically certain zones of the inner surface 12 of the preform, for example a nozzle to treat specifically the bottom 16 of the preform 10 and/or a nozzle to treat specifically a portion of the body 14 of the preform 10 with or without the introduction of the nozzle into the preform 10.

Numerous geometric nozzle shapes exist among which appear, for example, elongated nozzles having overall a finger shape that is typically suited to be introduced into the interior of a hollow body such as a preform 10 having a neck 18 with a reduced opening 20.

Also identified are the "stationary" nozzles of the rotary nozzles which can be driven in rotation around themselves.

As indicated previously, preferably, the nozzle 40 delivering the plasma is not introduced through the opening 20 of the neck 18 of the preform 10 during the third step (c), of treatment, and this to maintain an advantageously brief treatment time, particularly compatible with the rates of production of containers.

In short, so that there is a reduction of the hydrogen peroxide residue present on the inner surface 12 of the hollow body, it is necessary that the plasma come into contact with the hydrogen peroxide residue.

The length of the plasma between the outlet of the nozzle and the end of the plasma is at most 5 centimeters. Therefore, it is understandable that the use of plasma in connection with a bottle has not been satisfactory because the dimensions of the bottle and of the plasma do not match. Actually, to perform the treatment, it would be necessary to move the plasma in the bottle and that at the expense of the plasma application time during the third step (c) of plasma treatment which is less than one second (1 s), for example between 0.3 s and 0.6 s.

Furthermore, the shape of the plasma can be compared to a flame. As a consequence, this shape is even more compatible for treating the interior of a preform than for treating the interior of a bottle. Actually, in the case of a preform, the inner volume of the preform corresponds approximately to a cylinder whose diameter is between 10 and 40 millimeters. Consequently, the plasma licks the inner wall of the preform whereas in the case of a bottle, the plasma cannot lick the inner wall of the bottle over the entire length and/or over the entire periphery.

Figure 2:
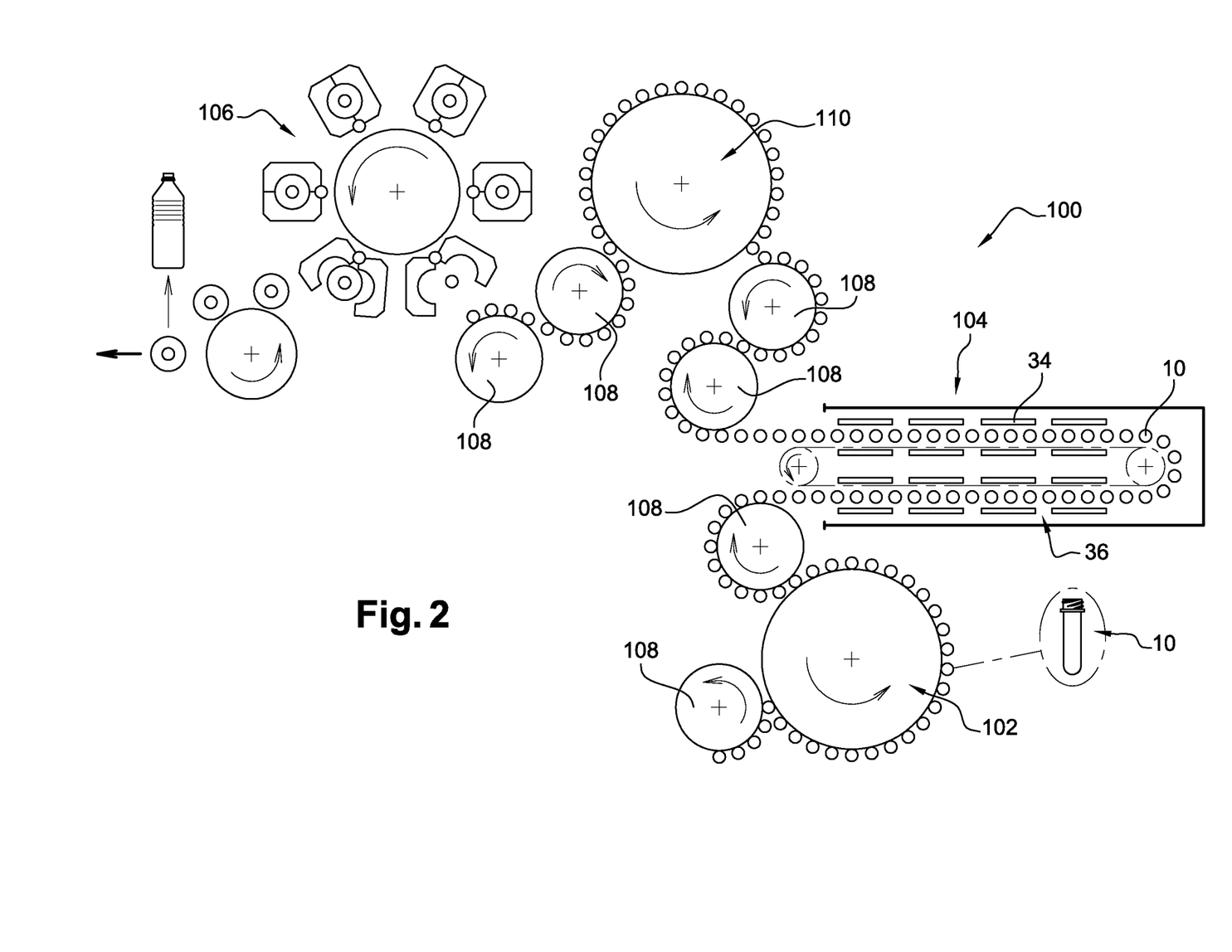
FIG. 2 is a diagrammatic view which represents an example of embodiment of an installation for manufacturing ultra-clean containers and which illustrates a plasma treatment unit for the preforms that is incorporated into the installation aimed at implementing the treatment process according to the invention.

Shown in FIG. 2 is an example of embodiment of an installation 100 for manufacturing containers from preforms 10 made of thermoplastic material.

FIG. 2 illustrates more specifically an installation 100 in which the treatment process which has just been described with reference to FIG. 1 would be used to treat preforms 10.

The manufacturing installation 100 has at least one unit 102 for treating the interior at least of the preforms 10 by application of hydrogen peroxide, a unit 104 for heating the preforms 10, a unit 106 for molding containers from the heated preforms 10.

The treatment unit 102 is, for example, able to treat preforms 10 by introducing hydrogen peroxide into the interior of at least one preform 10 to obtain a deposit by condensation of a film of hydrogen peroxide on the inner surface 12 of the preform 10.

The treatment unit 102 makes it possible to implement the first step (a), of treatment according to the process, as described previously with reference to FIG. 1a.

The heating unit 104 has at least one oven 36 provided with heating means 34 for implementing the step (b), for heating, according to the process of the invention and the thermal conditioning of the bodies 14 of the preforms 10 for their transformation into containers.

In a variant, not shown, the units 102 and 104 are one and the same unit, i.e., the injection of hydrogen peroxide is performed in the heating unit 104.

The unit 106 for molding containers (also called "blower") is intended to transform into containers the hot preforms 10 coming from the heating unit 104, by blow molding or by stretch blow molding which is accomplished in a mold.

The different units 102, 104 and 106 are in particular connected to each other by conveying devices 108, such as transfer wheels.

The installation 100 has at least one unit 110 for plasma treatment of the preforms 10 previously decontaminated with hydrogen peroxide so as to reduce the concentration of hydrogen peroxide residue in the preforms 10 and consequently in the containers obtained from such preforms 10.

The plasma treatment unit 110 is positioned upstream from the molding unit to reduce the concentration of sterilizing hydrogen peroxide residue in the interior of the preforms 10.

The plasma treatment unit 110 corresponds to the implementing of the step (c), of treatment, according to the process described with reference to FIG. 1c.

The step (c), of plasma treatment, can advantageously be implemented in an installation 100 for manufacturing containers without affecting its rates of production relative to the previously known units (for example, expressed in number of bottles per hour).

Actually, since the time for plasma treatment is less than one second, it is possible to incorporate such a unit 110 into the transfer path followed by the flow of preforms 10 through the installation 100, more specifically between the outlet of the heating unit 104 and the molding unit 106.

As shown in FIG. 2, the plasma treatment unit 110 is positioned in the installation 100 between the heating unit 104 and the molding unit 106, which thus makes it possible to manufacture containers from preforms 10 previously decontaminated with hydrogen peroxide as a result of the treatment unit 102 which, itself, is positioned upstream from the unit 104 for heating the preforms.

The fact of treating the preform with plasma between the unit for heating the preforms and the unit for molding containers causes a surprising effect which is to make possible the reduction of the major part of the hydrogen peroxide residue. This significant reduction of the hydrogen peroxide residue does not take place if the plasma treatment is completed after the unit for molding by pressurized blow molding. The inventor is aware that pressurized blow molding causes the absorption of a portion of the hydrogen peroxide residue by the hollow body made of thermoplastic material of the future container, and the other portion of the residue remains on the surface. Therefore, experience has shown that the plasma treatment performed on the bottle reduces only the hydrogen peroxide residue remaining on the surface, and has no effect on the hydrogen peroxide absorbed by the material of the future container.

In the case of a plasma treatment completed at the outlet of the heating unit, residual measurements of hydrogen peroxide have been taken twenty-four hours after the plasma treatment. The results show that the residual amount of hydrogen peroxide has diminished by fifty percent.

In the case of a plasma treatment completed at the outlet of the molding unit, hydrogen peroxide measurements have been taken also twenty-four hours after the plasma treatment. The results show that the residual amount of hydrogen peroxide has not decreased but has increased by two hundred percent. This is explained by the fact that the amount of hydrogen peroxide absorbed by the material is leached to the inner surface of the container.

Figure 3A:
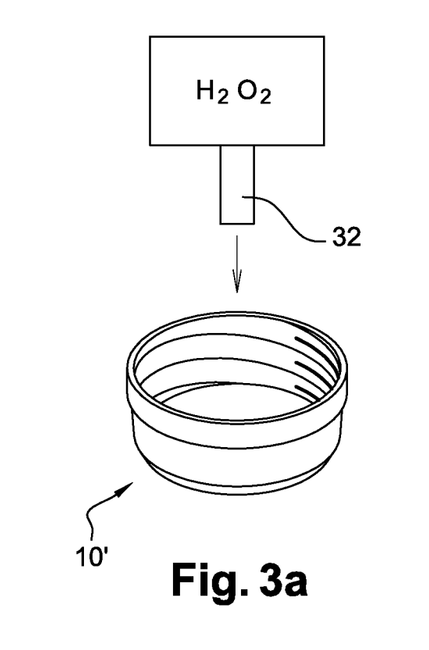
FIGS. 3a, 3b and 3c are views which diagrammatically represent the steps of the process for treating at least one cap made of thermoplastic material intended to close a container and which illustrate successively the treatment of the interior of the cap with hydrogen peroxide with the aim of decontaminating it, the heating with hot air of the cap and a plasma treatment of the interior of the cap so as to reduce the concentration of hydrogen peroxide residue there.
Figure 3B:
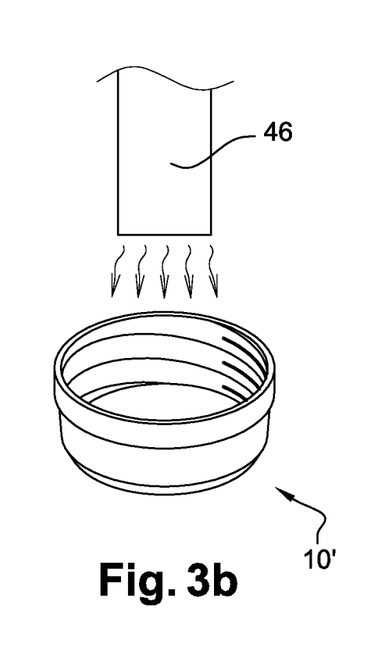
Figure 3C:
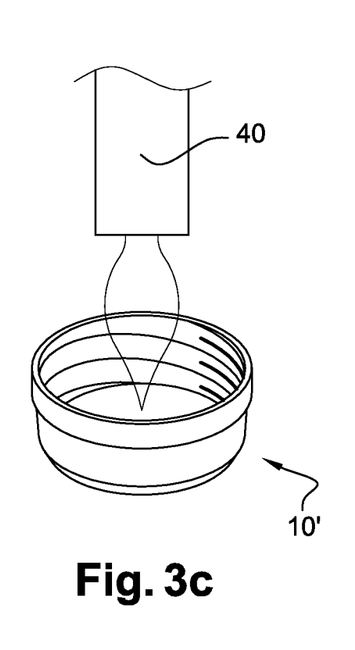

Shown in FIGS. 3a, 3b and 3c is a second example of application of the process of treatment according to the invention.

In this second example, the hollow body is a cap 10' made of thermoplastic material.

Such a cap 10' is intended to work, particularly by screwing, with a neck of a container so as to make it possible to close it.

The process for treating at least one cap 10' has successively at least the following steps:

(a) a first step, consisting in treating at least the interior of the cap 10' using hydrogen peroxide;

(b) a second step, consisting in heating said cap 10';

(c) a third step, consisting in treating the cap 10' with plasma to reduce its concentration of hydrogen peroxide residue.

Preferably, the cap 10' is treated with hydrogen peroxide in the same way as the preform 10 according to FIG. 1*a*, namely that a film of hydrogen peroxide mist is deposited by condensation on the interior of the cap 10'.

As shown with the first step (a) of FIG. 3*a*, the gas mixture comprising hydrogen peroxide is sprayed by an injection nozzle 32 in the direction of the interior of the cap 10'.

The second step (b), of heating the cap 10', is intended to thermally activate the hydrogen peroxide present so as to obtain the decontamination of the interior of the cap 10'.

Preferably, the second step (b), of heating, is completed with heating means 46 consisting of hot air.

In a variant, other equivalent heating means could also be used, such as, for example, infrared radiation, laser-type or else microwave heating means.

In the example illustrated in FIG. 3*b*, the heating means 46 to obtain hot air have, for example, heating electrical resistors and ventilation means to project the hot air in the direction of the cap or caps 10'.

The hot air delivered by the heating means 46 has a temperature which is higher than the thermal activation temperature of the hydrogen peroxide.

Once the step of decontamination of the cap 10' is completed, the third step (c) consists, as before for the preform 10, in applying a plasma delivered by a nozzle 40 to treat the cap 10' so as to reduce the concentration of hydrogen peroxide residue present on the cap 10'.

Of course, the representation made in FIGS. 3*a* to 3*c* is in no way limiting, and several caps 10' can be treated, simultaneously or not, particularly in line by means of a plurality of nozzles 40 for the application of the plasma, for example.

For the third step (c), of treatment of the cap 10', the parameters are advantageously similar to those described previously for the preform 10.

Preferably, the plasma is delivered by the nozzle or nozzles 40 which is or are positioned above the cap 10' so that the plasma alone penetrates the interior of the cap 10'.

The free end of the nozzle 40 for injection of the plasma is located at a distance (d) from the cap 10' which is less than one centimeter (1 cm), for example between 0.02 cm and 0.8 cm.

The time of application of the plasma during said third step (c), of treatment, is less than one second, for example between 0.3 s and 0.6 s.

By applying the treatment process according to the invention to preforms 10 and to caps 10', finished containers are obtained having an overall concentration of hydrogen peroxide which is advantageously reduced.

In the process for treating at least one hollow body, preform or cap, according to the examples of application described above, it is sought at the very least to reduce the concentration of hydrogen peroxide residue on the interior of said hollow body, said reduction being able to be obtained by treating with plasma all or only a portion of the interior of the hollow body.

The plasma can therefore be applied on only a portion of the inner surface 12 of a preform 10, for example preferably in the area of its neck 18 and/or of its bottom 16.

The invention claimed is:

1. A treatment process for use in manufacturing containers from at least one preform (10) made of thermoplastic material, said treatment process having successively at least the following steps:

(a) a first step, consisting in treating, using a first injection nozzle (32), at least the interior of a preform (10) using hydrogen peroxide ($H_2O_2$);
   (b) a second step, consisting in heating, using heating means (34, 46), a body (14) of said preform (10) to a molding temperature to make possible subsequent transformation of the body into a container; and
   (c) a third step, consisting in treating said preform (10), using a second injection nozzle (40), with plasma to reduce a concentration of hydrogen peroxide ($H_2O_2$) residue remaining in said preform (10) after heating, wherein the second infection nozzle (40) is not introduced through a neck opening of the preform (10).

2. The treatment process according to claim 1, wherein the first step (a), of treatment, consists in depositing by condensation a film of hydrogen peroxide at least on the interior of the preform (10) with the aim of decontaminating the interior.

3. The treatment process according to claim 2, wherein the second step (b), of heating, consist in heating the preform (10), in which hydrogen peroxide is found, to a determined temperature which is higher than a thermal activation temperature of the hydrogen peroxide, where the thermal activation temperature is a temperature at which hydrogen peroxide begins to transition from a liquid state to a gaseous state.

4. The treatment process according to claim 2, wherein the second injection nozzle (40) is positioned so that the plasma alone penetrates the interior of the preform (10).

5. The treatment process according to claim 2, wherein the plasma application time during the third step (c), of treatment, is less than one second (1 s).

6. The treatment process according to claim 1, wherein the second step (b), of heating, consists in heating the preform (10), in which hydrogen peroxide is found, to a determined temperature which is higher than a thermal activation temperature of the hydrogen peroxide, where the thermal activation temperature is a temperature at which hydrogen peroxide begins to transition from a liquid state to a gaseous state.

7. The treatment process according to claim 6, wherein the second injection nozzle (40) is positioned so that the plasma alone penetrates the interior of the preform (10).

8. The treatment process according to claim 6, wherein the plasma application time during the third step (c), of treatment, is less than one second (1 s).

9. The treatment process according to claim 1, wherein the second injection nozzle (40) has a free end positioned so that the plasma alone penetrates the interior of the preform (10).

10. The treatment process according to claim 9, wherein the free end of the second injection nozzle (40) is located at a distance (d) from the preform (10) which is less than one centimeter (1 cm).

11. The treatment process according to claim 9, wherein the second injection nozzle (40) is positioned so that the plasma alone penetrates the interior of the preform (10).

12. The treatment process according to claim 9, wherein the plasma application time during the third step (c), of treatment, is less than one second (1 s).

13. The treatment process according to claim 1, wherein the plasma application time during the third step (c), of treatment, is less than one second (1 s).

14. The treatment process according to claim 1, wherein the heating means is selected from a group consisting of infrared radiation (IR) heating means, laser-type heating means, and hot air heating means.

* * * * *